US008771331B2

(12) United States Patent
Geibel

(10) Patent No.: US 8,771,331 B2
(45) Date of Patent: Jul. 8, 2014

(54) WRAP FOR APPLYING THERMAL THERAPY TO A BODY PART

(76) Inventor: Craig Geibel, San Marcos, CA (US)

(*) Notice: Subject to any disclaimer, the term of this patent is extended or adjusted under 35 U.S.C. 154(b) by 405 days.

(21) Appl. No.: 12/879,942

(22) Filed: Sep. 10, 2010

(65) Prior Publication Data
US 2011/0066218 A1 Mar. 17, 2011

Related U.S. Application Data

(60) Provisional application No. 61/241,867, filed on Sep. 12, 2009.

(51) Int. Cl.
*A61F 7/02* (2006.01)
(52) U.S. Cl.
USPC ........................................... 607/112; 607/114
(58) Field of Classification Search
CPC .............. A61F 7/02; A61F 2007/0228; A61F 2007/023
USPC .................. 607/112, 96, 108, 114; 62/530
See application file for complete search history.

(56) References Cited

U.S. PATENT DOCUMENTS

| 4,033,354 A * | 7/1977 | De Rosa ........................ 607/108 |
| 4,347,848 A | 9/1982 | Hubbard et al. |
| 4,586,506 A * | 5/1986 | Nangle .......................... 607/112 |
| 4,951,666 A | 8/1990 | Inman et al. |
| 5,020,711 A * | 6/1991 | Kelley .......................... 224/222 |
| 5,052,387 A | 10/1991 | Natali |
| 5,179,942 A * | 1/1993 | Drulias et al. ............. 128/101.1 |
| 5,427,563 A * | 6/1995 | Manning ......................... 450/79 |
| 6,440,159 B1 | 8/2002 | Edwards et al. |
| 6,589,272 B1 | 7/2003 | Sheikh |
| 6,830,582 B1 | 12/2004 | Reid, Jr. et al. |
| 6,936,018 B2 | 8/2005 | Chalek |
| 7,012,169 B2 | 3/2006 | McDevitt et al. |
| 7,041,124 B2 | 5/2006 | Purcell |
| 7,060,086 B2 | 6/2006 | Wilson et al. |
| 7,065,983 B2 | 6/2006 | Trinh et al. |
| 7,096,687 B2 | 8/2006 | Trinh et al. |
| 7,264,602 B1 | 9/2007 | Longsworth |
| 7,264,630 B1 | 9/2007 | Webb |
| 7,291,164 B2 | 11/2007 | Peterman et al. |

(Continued)

OTHER PUBLICATIONS

Merrick et al., "Cold Modalities With Different Thermodynamic Properties Produce Different Surface and Intramuscular Temperatures", Jan.-Mar. 2003.*

(Continued)

*Primary Examiner* — Linda Dvorak
*Assistant Examiner* — Jocelyn D Ram
(74) *Attorney, Agent, or Firm* — Eleanor M. Musick; Procopio, Cory, Hargreaves & Savitch LLP

(57) ABSTRACT

A wrap for applying thermal therapy to a body part includes a substantially liquid-tight, flexible polymer bag for containing a thermal agent which is attached to a wrap body formed from a non-expandable material. The bag is fastened to the wrap body such that the fastening area is 25% or less than the area of the bag. A pair of wings formed from an expandable, retractable material extends from each of opposite sides of the wrap body. Releasable fasteners are attached at the ends of at least two wings to attach to the ends of the opposite wings to secure the bag over the body part.

20 Claims, 4 Drawing Sheets

(56) References Cited

U.S. PATENT DOCUMENTS

| | | |
|---|---|---|
| 2002/0073731 A1 | 6/2002 | Bride-Flynn |
| 2003/0124277 A1* | 7/2003 | Agarwal et al. .............. 428/35.2 |
| 2005/0049537 A1* | 3/2005 | Purcell et al. ................... 602/75 |
| 2005/0192524 A1* | 9/2005 | Lipshaw et al. ................. 602/62 |
| 2007/0106354 A1 | 5/2007 | Carstens |
| 2008/0188786 A1* | 8/2008 | Hickling ........................ 602/26 |
| 2008/0195012 A1* | 8/2008 | Miros et al. .................... 602/26 |
| 2009/0005718 A1* | 1/2009 | Lightbourne ................... 602/75 |
| 2009/0120126 A1* | 5/2009 | Mew .............................. 62/530 |

OTHER PUBLICATIONS

International Search Report and Written Opinion for PCT/US2010/048513 issued Jun. 7, 2011, 11 pages.

\* cited by examiner

WRAP FOR APPLYING THERMAL THERAPY TO A BODY PART

RELATED APPLICATIONS

This application claims the priority of U.S. provisional application No. 61/241,867, filed Sep. 12, 2009, which is incorporated herein by reference.

FIELD OF THE INVENTION

The present invention relates to a cold therapy apparatus. More specifically, the invention relates to a reusable, disposable bag that can be filled with ice that is affixed to a flexible and expandable wrap that can be wrapped around an area of a body to apply cryotherapy.

BACKGROUND OF THE INVENTION

Cryotherapy, which is the application of cold to an injured area, is a treatment used to manage the magnitude of the inflammatory process, blood flow, initial swelling, secondary injury and pain. The use of ice packs is widespread because of their effectiveness, convenience, low cost, and ease of transportation.

Several approaches have been taken to apply cold therapeutic wraps to a sore muscle or joint after a workout or injury. The typical methods of providing this type of cold therapy involve filling a bag with ice, applying the bag of ice to a part of the body and wrapping the bag onto the body with an elastic bandage or plastic wrap similar to that used for packing. In athletic activities involving teams of individuals, multiple team members may enter the locker room at the same time, overwhelming the team trainer, who must attend to a large number of athletes within a narrow window of time when it is critical to apply the ice as quickly as possible. In this situation, a quickly filled, easily applied method of administering cold therapy is essential. An important component of ice therapy involves application of compression at the target area, i.e., the joint or muscle to be treated, to induce vasoconstriction to limit inflammation and swelling and reduce pain. Thus, simply laying the ice bag on top of the area is not sufficient to obtain the full benefit of the cold therapy—a securing means must be used. Another important feature of the wrap is the ability of the athlete to move around without removing or displacing the ice bag or losing the compression at the desired area.

A number of devices for applying ice to injuries or to prevent injuries have been described in patents. Hubbard et al. (U.S. Pat. No. 4,347,848) and Inman et al. (U.S. Pat. No. 4,951,666) each disclose a small disposable ice pack with two pairs of tie strings for tying the ice bag onto a limb. The small bag further includes a closure to keep the ice within the bag. While this design provides a disposable ice bag that can be secured to a body part, the simple strings cannot be tied in a way to apply adequate compression to the target area, nor can they ensure that the ice will stay in place if the person moves around. Furthermore, if the cold therapy is to be applied to an arm, the assistance of a second person is required because the person receiving treatment would be unable to tie the strings himself or herself.

Natali (U.S. Pat. No. 5,052,387) discloses a cold pack for wrapping injured limbs, which consists of rectangular layers of thermoplastic sheet with one or more bags formed at one end of the rectangle and a wing with an adhesive strip at the other end. The bag is filled with ice and the wing is wrapped around the arm or leg and secured in place with the adhesive strip. While this invention provides a disposable ice bag that can be secured to the limb, because it is formed from plastic sheet and does not stretch, it is not capable of applying focused compression at the target site, nor will it stay in place if the person moves around. The adhesive strip allows minimal re-positioning of the bag once the wing is adhered onto the bag.

U.S. Pat. No. 5,887,437 of Maxim describes a self-adhering cold pack that includes an adhesive on the bottom side of a layered structure that includes a bag for retaining a cooling agent. The light adhesive on the bottom of the bag is intended to stick directly to the user's skin. Such a design may be helpful for simple cold therapy, but it is incapable of applying a focused compression and further has the disadvantage of a single use.

Reid, Jr. et al. (U.S. Pat. No. 6,830,582) discloses a thermal wrap for body member. Embodiments of this invention include a bag with straps having adhesive backed strips, and a bag with a wing having adhesive on one end. While this invention provides a disposable ice bag that can be secured to the user, like Natali, the design suffers the drawbacks of the previously-described devices. The straps of the first embodiment, like the tie strings, cannot maintain compression where needed and will not hold the bag in place when the person moves. In the single winged configuration, because the wing is non-elastic, it will not apply a focused compression and would not stay in position when the person moves. The adhesive strips allow minimal re-positioning of the bag once they are adhered onto the bag.

Bride-Flynn (U.S. Pat. No. 6,470,705) discloses a disposable ice pack that is similar in basic design to the packs described by Hubbard et al. and Inman et al., having a bag with pairs of straps or strings extending from the bag's corners. This design, therefore, suffers the same drawbacks that the Hubbard et al. and Inman et al. designs do.

Other approaches to devices for applying cold therapy include gels and other chemical cooling agents that are enclosed within a bandage-like structure and activated by breaking a seal between compartments holding the reactants. While such devices may be useful for short term cold therapy, athletes and others who require repeated continuous application of ice for relatively long periods of time, e.g., 20 minutes of every hour for several hours, they are quite impractical and potentially dangerous since the temperature may not be well controlled and can result in frostbite if held in place for extended periods. Furthermore, such products are for single use only, and not for repeated uses.

The need remains for a cold therapy apparatus that is quickly filled, quickly applied, capable of applying focused compression, reusable for a number of applications while still being disposable. The ideal device would further be cost effective to produce and dispense to allow for optimal efficiency in use and convenience. The present invention is directed to such a need.

BRIEF SUMMARY OF THE INVENTION

It is an object of the present invention to provide a multi-use, disposable cold therapy device that is easy to fill with a cooling agent and stably apply to the target area of the body.

It is another object of the invention to provide a cold therapy device that applies focused compression to the desired target location.

Still another object of the invention is to provide a thermal therapy device that is held in place with sufficient stability to allow the user to move with relative freedom while continuing treatment.

In an exemplary embodiment, a wrap for applying thermal therapy to a body part includes a substantially liquid-tight, flexible polymer bag for containing a thermal agent which is attached to a wrap body formed from a non-expandable material. The bag is fastened to the wrap body such that the fastening area is 25% or less than the area of the bag. A pair of wings formed from an expandable, retractable material extends from each of opposite sides of the wrap body. Releasable fasteners are attached at the ends of at least two wings to attach to the opposite wings to secure the bag over the body part.

In one aspect of the invention, the inventive cold therapy device comprises a waterproof bag that is attached to a soft fabric or fabric-like cover that has two or more expandable elasticized or elastomeric wings extending from opposite sides of the ice bag. In one embodiment, the cover may be formed from one or more sheets of breathable material that permits gases, such as water vapor, to escape. For example, the sheets may be composed of a microporous polymer film or a nonwoven fabric that has been coated or otherwise treated to impart a desired level of liquid impermeability. For example, a suitable microporous film can be a polyolefin film. In general, appropriate materials include those used in the manufacture of disposable diapers and undergarments, which materials are well known in the art. The use of sturdy, inexpensive materials provides a wrap that is reusable, if desired, yet disposable after multiple uses.

The wings may be formed from an elastomeric material such as a neck-bonded laminate (NBL) or stretch-bonded laminate (SBL) material. A stretch bonded laminate refers to a composite material having at least two layers in which one layer is a nonelastic gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended.

The wings have re-fastenable securing mechanisms near their outer edges to allow for quick placement over the target area of the body, to be secured in a single motion. In a preferred embodiment, the securing mechanisms are hook-type fasteners, e.g., VELCRO®, which extend from the wings on tabs or flaps, although the fasteners may be affixed directly on the main area of the wing. Similar constructions are used in disposable diapers. The flexible and expandable nature of the wings allows them to move with the user while maintaining the desired compression and, at the same time, minimizing the potential of reducing circulation if the wrap is secured too tightly. The area of attachment between the bag and the cover is less than the full area of the bag, preferably one-half or less of the area of the bag, to allow focusing of the compression at a desired target location. Most preferably, the attachment area is on the order of 10% or less of the length of the wings.

In one aspect of the invention, the reusable, disposable thermal therapy device includes a bag that can be ideally filled with ice, but can also be filled with a cold pack, hot pack or other thermal therapeutic medium that provide healing, soothing or other benefits to the user. The bag can be configured as either a pleated or non-pleated configuration allowing for differing amounts of ice to be placed within the bag depending upon the use of the device. The ice bag may also include a closeable or re-closable lip, tab or other sealing mechanism that allows filling and/or re-filling of the bag. Multiple bags may also be incorporated to provide cold therapy on two locations on opposite sides of a leg or arm.

In another aspect of the invention, the cold therapy device includes securing wings configured in a variety of shapes and lengths. The different shapes may include long and short wings, and multiple wings from the same side of the bag. In a preferred embodiment, partially overlapping wings extend from each of two opposite sides of the bag. Each wing has its own fastening mechanism. This configuration allows for contouring of the wrap around the user's joint, e.g., knee, elbow, shoulder, etc., to provide a customized fit to ensure continued compression and stability during movement. The variable wing lengths and configurations make the device ideal for wrapping around a flexible joint such as an elbow as well as a non-flexible area such as the upper leg. A combination of long and short wings can also be used to wrap around the chest and arm respectively without excessive material being trimmed.

Still another object of the invention is to provide a cold therapy device in an easily-dispensed configuration, for example, as a roll, a box of multi-layered sheets, or in a pop-up dispenser, which allows a trainer to quickly prepare a number of the cold therapy wraps to accommodate a large number of athletes in a short period of time.

Various objects, features, aspects, and advantages of the present invention will become more apparent from the following detailed description of preferred embodiments of the invention, along with the accompanying drawings in which like numerals represent like components.

DETAILED DESCRIPTION OF EXEMPLARY EMBODIMENTS

Figure 1:
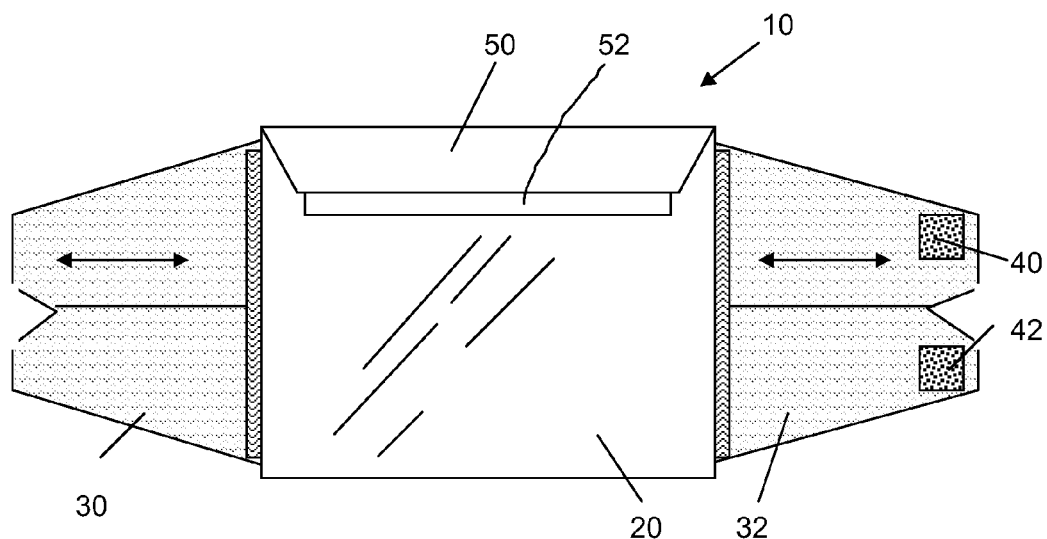
FIG. 1 is a plan view of a first embodiment of the inventive cold therapy bag.

FIG. 1 shows a first embodiment of the disposable cold therapy bag with elastic wings extending from both sides of the bag. This illustrates the cold therapy device 10 in its basic configuration. The central bag 20 is a flexible bag that is sealed on three sides with a sealable fourth side, assuming the bag is square or rectangular. The shape of the bag is not intended to be limited to a square, and other shapes may be used, with the edges of the bag sealed except for an openable section that permits ice or other thermal agent to be inserted and sealed within the bag.

The bag can be fabricated from a number of different materials including but not limited to polymers such as PVC, Polyethylene, Polyolefin, ABS (acrylonitrile butadiene styrene) or other material that is waterproof and capable of holding ice or other thermal agent without substantial leakage. The fourth side (or other open edge) has a tab or flap 50 or other sealing means, such as interlocking channels (e.g., as used in ZIP-LOC® bags) that will create a substantially liquid-tight seal when closed. The open side allows the bag to be filled with variable levels of ice or other thermal agents. It is also contemplated that the bag can be filled with a heated pack or other warm or hot pack, or a cooling agent such as an encapsulated gel or other chemical cooler. An adhesive, VELCRO® hook and pile fastener, or other semi-permanent or permanent closing component 52 is located on the tab of the bag. It is also contemplated that the tab can be replaced with a zipper, re-sealable or similar closing system. Another contemplated closure is a bag with an extended opening that can be tied shut.

The outer surface (non-skin-contacting side) of the bag may be covered with a fabric or other covering that has a pile-like, or fuzzy texture that will mesh with the hook portion of a VELCRO®-type fastener or similar closing component 52 to seal the bag. In one embodiment, wings 30 and 32 extend from opposite sides of the bag to provide means for applying the bag to the target area (joint or muscle) of the user. In a preferred embodiment, the bag 10 is attached to the inner surface of a separate wrap or cover, with the wings extending from the cover (see, e.g., FIGS. 2 and 3). The wings are fabricated from an elastic material that allows them to be stretched and secured, wrapping firmly around the target area. Material that is contemplated for this purpose includes but is not limited to rubber, spandex, LYCRA® elastic, and other materials that accomplish the similar function. These materials can be stretched many times their original length, and return to their original length. The wings may further be covered, coated or bonded with a fabric cloth or cotton material that allows VELCRO® hooks or other similar temporary securing device 40, 42 to releasably fasten the wings together. Prototypes have been fabricated using the elastic side panels from disposable diapers. These components include the elastic expandable-retractable portion, and the fastening portion. Other contemplated methods include the adhesive bonding components that are used to secure other types of disposable diapers.

For use of the cold therapy bag in the example of the team trainer, multiple bags can be pre-filled with ice or other media and stored in a cold area, or on a table. When the bags are needed, each bag can be quickly positioned on the area needing therapy, the wings grasped, stretched and pulled over and around the part of the body and secured onto the other wing. If the bag needs to be re-filled, moved, or the tension changed, the ends of the wings can be pulled, dislodging the bond between the retaining mechanism(s) 40, 42, filled, and replaced on the part of the body.

FIGS. 2 through 4, 7 and 8 illustrate exemplary embodiments of the thermal treatment wrap, which includes a waterproof bag 300 that is attached to a soft fabric or fabric-like cover body 302. Two or more expandable elasticized or elastomeric wings 304, 306, 308, 310 extend from opposite sides of the body. In one embodiment, the cover body 302 may be formed from one or more sheets of breathable material that permits gases, such as water vapor, to escape. For example, the sheets that form the cover may be formed from a microporous polymer film or a nonwoven fabric that has been coated or otherwise treated to impart a desired level of liquid impermeability while still being breathable. A suitable microporous film can be a polyolefin or polyethylene film. Preferably, the material used for body 302 is not expandable, or is minimally expandable, but still pliable and sufficiently soft to be comfortable when it comes into contact with the user's skin. It should be noted that expandability of the body 302 may impact the ability to focus the desired compression. In general, appropriate materials include those used in the manufacture of disposable diapers and undergarments, such that selection of a suitable material will be readily apparent to one of skill in the art. Selection of such sturdy, inexpensive materials provides the advantage that the wrap is reusable for a number of times, if desired, yet inexpensive enough to be discarded after multiple uses.

The wings 304, 306, 308 and 310 may be formed from an elastomeric material such as a neck-bonded laminate (NBL) or stretch-bonded laminate (SBL) material. "Neck-bonded laminate" refers to a composite material having at least two layers in which one layer is a necked, non-elastic layer and the other layer is an elastic layer, thereby creating a material that is elastic in the cross-direction. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, which are incorporated herein by reference. A stretch bonded laminate refers to a composite material having at least two layers in which one layer is a nonelastic gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen et al., which is incorporated herein by reference. For increased strength, it may be desirable to provide multiple layers of the laminate as long as the appropriate degree of elasticity is retained.

Figure 3:
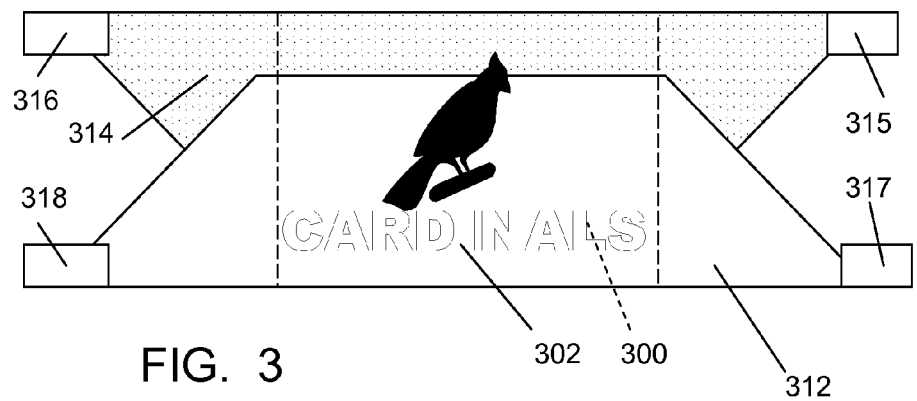
FIG. 3 is a plan view of the outer surface of the embodiment of FIG. 2.
Figure 4:
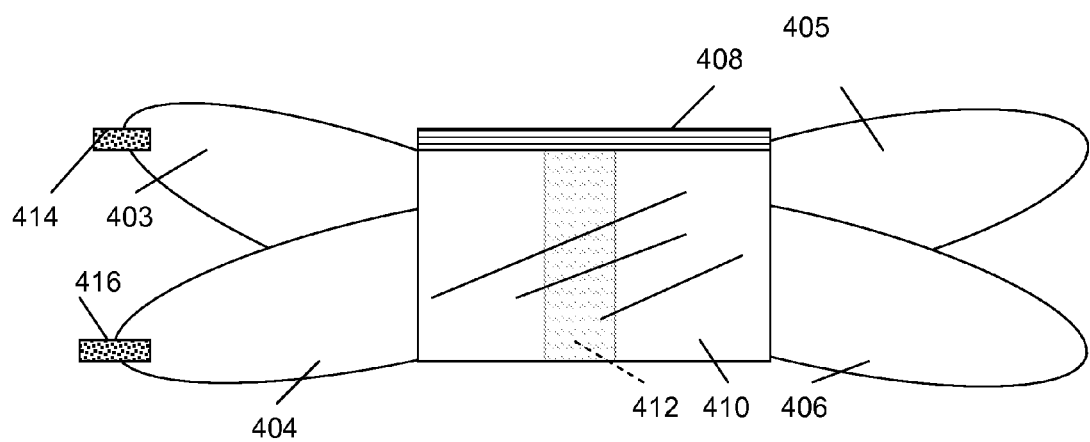
FIG. 4 is plan view of one embodiment of the disposable cold therapy bag with butterfly-like elastic wings extending from opposite sides of the bag.

The wings can be integrally formed with the body 302 as continuous sheets such that two (or more, if more wings are to be formed) partially overlapping trapezoid-shaped sheets (which are attached together to define body portion 302) are used as shown in FIG. 3, or they may be attached thermally, ultrasonically or otherwise adhered to provide a permanent attachment between the body 302 and the wings. Even in an embodiment where the wings and wrap body may be integrally formed, the wing portions will still be formed from expandable, retractable material while the body portion will be non- or minimally expandable. Such combinations in an integrated sheet structure are well-known in the manufacture of disposable diapers. Specifically, the wing portions are formed from the elastic/non-elastic composite while the body portion is completely non-elastic. In a preferred embodiment, the wing portions are independent of each other, i.e., the overlapping sheets should be not attached to each other beyond the body 302 portion of the cover. This provides greater adjustability for fitting the wrap to the desired area of treatment. It should be noted that while the shapes that are shown in the figures are trapezoids, additional shapes may be used including rounded or truncated trapezoids, ovals and other polygons, boomerang shapes, as shown in FIG. 4, and other shapes, symmetrical or not, that when combined are capable of defining wings extending from opposite sides of a main body to which the ice bag is attached. It should also be noted that while the examples that are described herein and illustrated in the drawings show two wings extending from opposite sides of the wrap body portion, three or more wings may be created by adding overlapping sheets while observing the principle that the wing portions are independent of each other and formed are from expandable/retractable material.

Figure 2:
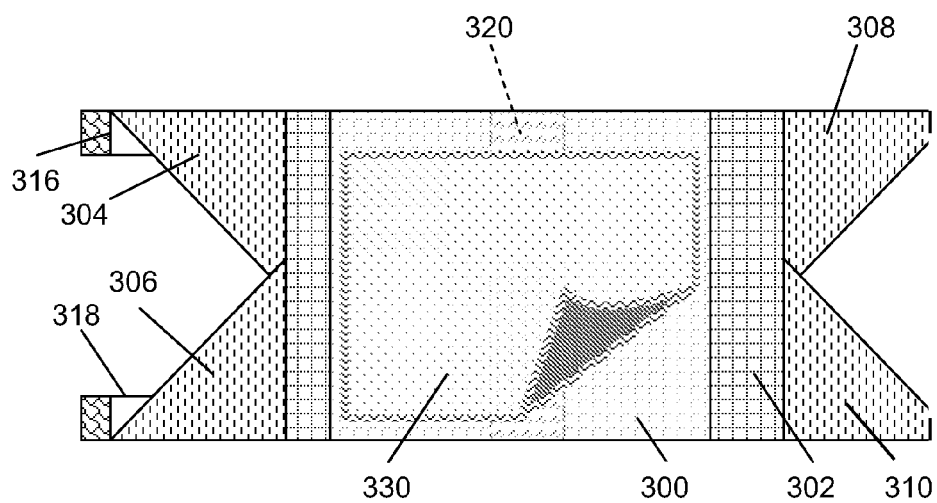
FIG. 2 is a plan view of the inner surface of a second embodiment of the invention with the bag attached to a wrap/cover.

The wings have re-fastenable securing mechanisms near their outer edges to allow for quick placement over the target area of the body, to be secured in a single motion. In a preferred embodiment, the securing mechanisms are hook-type fasteners, e.g., VELCRO®, which extend from the wings on one side of the wrap on tabs or flaps 316, 318 (as shown in FIG. 2) to releasably attach to the outer surface of the opposing wing, or from both sides of the wrap (e.g., tabs 315-318) as shown in FIG. 3, which allows the wings to overlap from either side, depending on what is more convenient for the user. Although tabs are shown extending slightly from the wings, the fasteners may also be affixed directly to the main area of the wing. Preferably, but not necessarily, the hook-type fasteners will be able to capture pile-like fibers within the wing material of wings 308 and 310 such that a separate, additional piece of pile material is not required. This provides greater flexibility in fitting the wrap to the user's needs since the hooks can be attached anywhere within the body of the wings. Similar constructions are found in disposable diapers, including those described in U.S. Pat. No. 5,399,219 issued Mar. 21, 1995 to Roessler et al.; U.S. Pat. No. 5,540,796 to Fries; and U.S. Pat. No. 5,595,618 to Fries. An example of methods for assembling such combinations can be found in U.S. Pat. No. 6,730,188 of Sanders. Each of the above-identified patents is incorporated herein by reference. The flexible and expandable nature of the wings 304, 306, 308 and 310 allows them to move with the user while maintaining the desired compression, at the same time minimizing the potential of reducing circulation if the wrap is secured too tightly.

Figure 7:
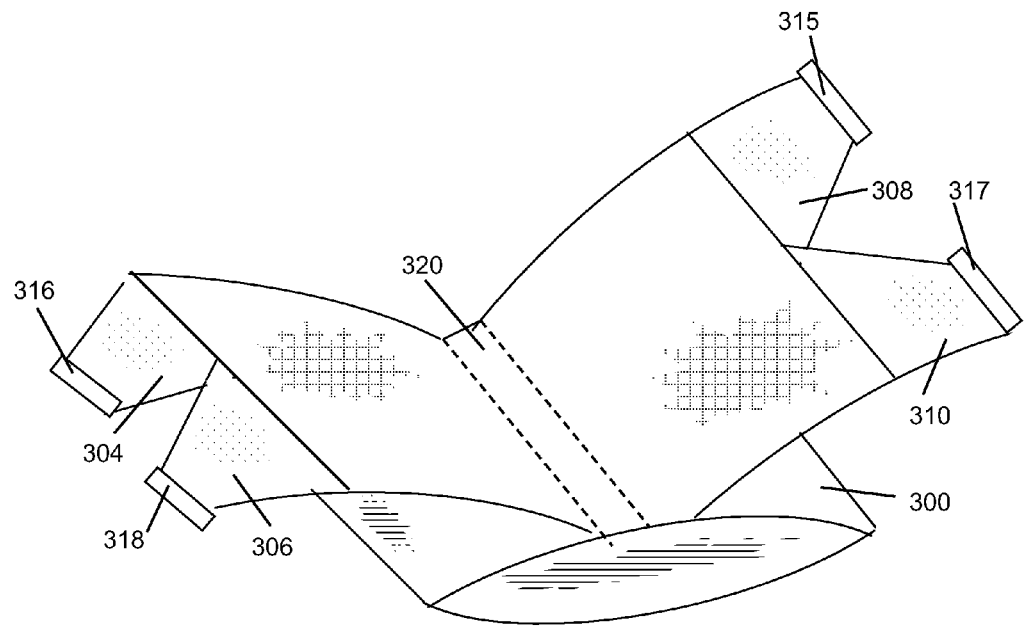
FIG. 7 is a perspective view of one embodiment of the cold therapy bag.

Bag 300 is attached to the body 302 of the wrap using a thermal process, e.g., a heat weld, adhesive, or other fastening device or method as is known in the art. The area of attachment 320 between the bag and the body portion 302 is less than the full area of the bag, as shown in FIGS. 2 and 7. Preferably, attachment area 320 is one-half or less of the area of the bag, more preferably, 25% or less, to allow the compression to be focused at a desired target location by placing the attachment area 320 directly over the desired treatment area. In the preferred embodiment, the attachment area 320 will be on the order of 10% or less of the length of the body portion.

An optional absorbent, moisture-retaining material 330 may be removably attached to the inner, skin contact surface of bag 300, as shown in FIG. 2. The absorbent material 330, which may be terry-cloth, microfiber material or other similar natural or synthetic material, may be moistened with water to allow the user to receive wetted-cold therapy. Recent studies have shown that wetted therapy is more effective than either cubed ice or crushed ice in lowering surface temperature and maintaining the lower temperature during recovery. (See, e.g., Dykstra, et al, "Comparisons of Cubed Ice, Crushed Ice, and Wetted Ice on Intramuscular and Surface Temperature Changes", *Journal of Athletic Training*, 2009, 44(2):136-141). The absorbent material 330 may be attached via an adhesive backing, by hook-and-pile fasteners, by plastic snaps or other appropriate fasteners that preferably will not contact the user's skin or lessen the user's comfort.

FIG. 4 illustrates a butterfly-wing-like construction formed from two overlapping boomerang shaped sheets of cover material. As in the previous embodiment, the main body of the cover where the two sheets are bonded together is a soft, flexible, but non-elastic material that is adhered to the bag 410 along a relatively narrow strip 412 to allow compression to be focused at the desired location. Note that the strip 412 need not be centered on the bag, but can be located off-center or near one side edge of the bag. Wings 403, 404, 405 and 406, formed from elastic materials with limited expandability as described above, extend from the body with releasable fasteners 414, 416 located at or near the distal ends of at least two of the wings, so that when the device is wrapped around the user's limb, the fasteners 414, 416 will contact and attach to the opposite wing. As above, the overlapping portions of the wings are preferably not attached to each other to allow greater flexibility in positioning of the wrap, adapting the wrap to curves and bends depending on where it is applied. The bag 410 as illustrated includes a zipper-like closure 408 such as those that are commonly used in food storage bags, such as ZIPLOC® brand bags, and other types of storage bags.

Figure 5:
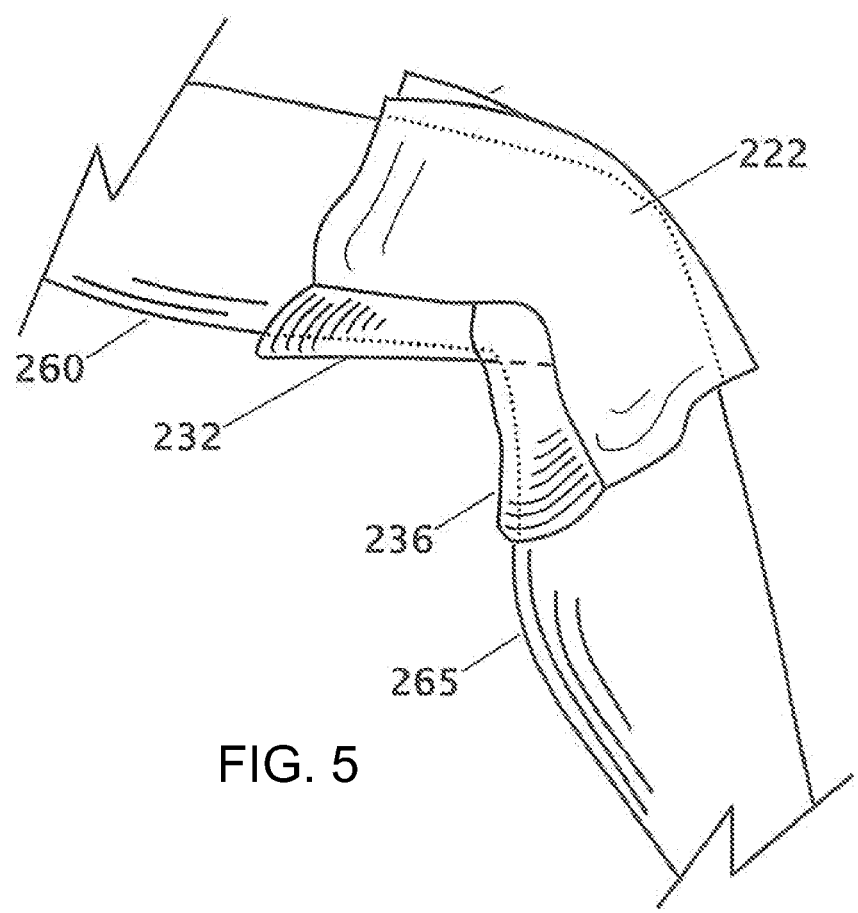
FIG. 5 is a side view of the embodiment of FIG. 4 applied to the user's knee.

FIG. 5 is side view of the embodiment from FIG. 4 shown on the knee of a person. The bag 222 is shown filled and placed over the knee of the user. Two of the wings of the cold therapy bag 230 and 232 are shown wrapped around the upper portion of the leg 260 and the second set of wings 234 and 236 are shown wrapped around the lower part of the leg 265.

Figure 6:
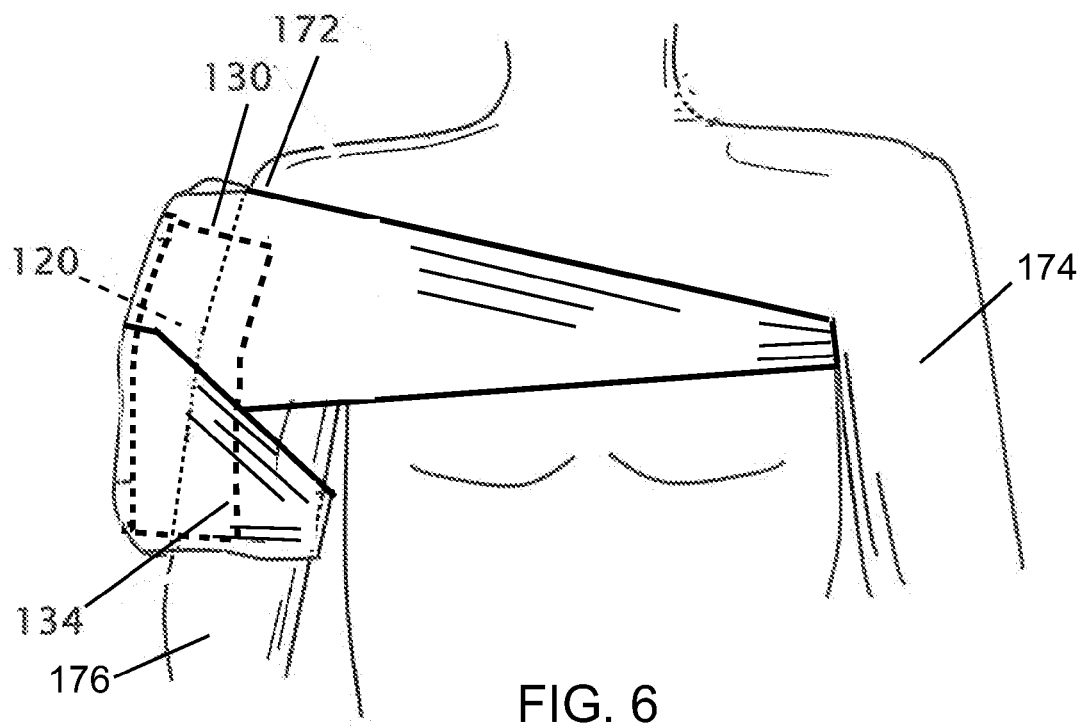
FIG. 6 is a front view of an alternative embodiment of the invention applied to the user's upper arm.

FIG. 6 shows an alternative embodiment of the disposable cold therapy wrap applied for treatment of the user's shoulder. In this embodiment, the elastic wings 130 and 134 are asymmetric in length to allow a portion of the wrap to be secured around a relatively large diameter body part, e.g., the torso. In this example, one set of wings, 130 at the front and its counterpart wing at the back (not shown), which extend from the upper portion of the wrap body as illustrated, are significantly longer than wing 134 and its counterpart (not shown) at the lower portion of the wrap body. This configuration of different length wings allows the cold therapy bag to be used on the shoulder, upper arm or other part of the anatomy where both short and long wings are appropriate to facilitate stable positioning of the ice bag 120 over the treatment area. Each of the wings includes the releasable fastening means that were previously described, e.g., hook connectors on one of each pair of wings or mating hook-and-pile fasteners on each pair of wings. In the illustrated example, the wrap is positioned with the bag in contact with the upper arm of a user. The long wing 130 and its counterpart are wrapped around the upper arm 172 and across the user's chest to be secured under the user's other arm 174. Shorter wing 134 and its counterpart are wrapped around the arm 176 of the user and secured with the fastener(s).

Figure 8:
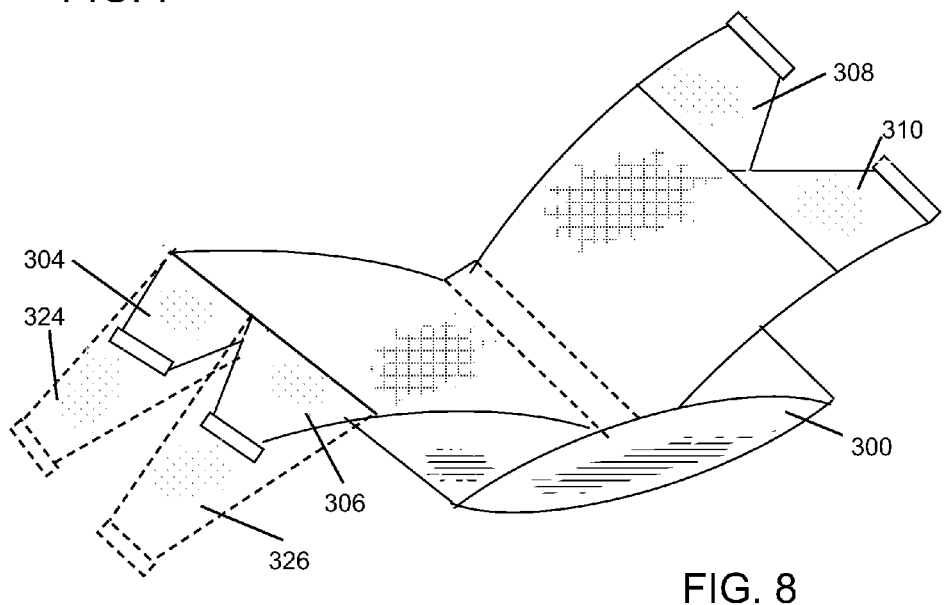
FIG. 8 is a perspective view of alternative embodiment of the cold therapy bag.

The embodiment of the inventive wrap illustrated in FIG. 8 is a variation on the asymmetric wings, providing the choice of the standard shorter wings 304, 306 as described in the previous embodiments, or longer wings 324, 326 on one or both sides of the wrap. (Only one side is illustrated.) With this embodiment, a single wrap may be adapted for use on different body parts by selecting the appropriate length wings. The longer wings 324, 326 are layered beneath, i.e., on the inside of, the shorter wings 304, 306, so that they can be rolled up and tucked under the shorter wings when not in use. Alternatively, the longer wings can simply be cut off if the user knows that they will not be using the wrap for any larger diameter parts of the body. The multiple length wings provides a versatile all-in-one joint bag, allowing a knee wrap to become a shoulder wrap by using the longer wings on one side or a back wrap by extending the longer wings on both sides to wrap around the user's torso. Optional additional straps can be provided for attachment using the existing fasteners 315, 316, 317 and 318 for even further extension. The optional straps would preferably have mating fasteners at each end, e.g., hook, or hook-and-pile fasteners, to allow easy attachment to the existing fasteners.

The expandable wings of the inventive wrap provide the ability to apply compression to the area being treated while allowing the person to walk or move about with the cold therapy wrap secured to the treatment area. Any of the above-described embodiments can be customized by imprinting a team name and/or logo (as shown in FIG. 3), the name of a sponsor, such as a shoe or athletic clothing company, or a sports drink name, to name a few examples, on the outer surface of the wrap. In this manner, the wrap can also serve the purpose as a marketing tool. Alternatively, images of national, state or organizational flags, cartoon characters or other images can be imprinted on wrap to allow the user to express themselves.

Exemplary embodiments and applications for a disposable cold therapy wrap having expandable, retractable wings have been described. It should be apparent to those skilled in the art that additional modifications are possible without departing from the inventive concepts herein, which are limited solely the appended claims.

The invention claimed is:

1. A wrap for applying thermal therapy to a body part comprising:
   a bag for containing a thermal agent, the bag having a bag area;
   a non-expandable wrap body having a first body end and a second body end separated by a body length, and a body width;
   a fastening strip for attaching the bag to the wrap body, the fastening strip extending across the body width and having a fastening area much less than the bag area;
   a first pair of wings comprising a first upper wing and a first lower wing formed from an expandable, retractable material extending from the first body end, wherein each of the first upper wing and the first lower wing has a proximal end with a first wing width adjacent the first body end and tapers to a narrower first distal end, wherein the proximal end of the first upper wing partially overlaps the proximal end of the first lower wing to define a combined first wing width substantially equal to the body width;
   a second pair of wings comprising a second upper wing and a second lower wing formed from an expandable, retractable material extending from the second body end, wherein each of the second upper wing and the second lower wing has a proximal end with a second wing width adjacent the second body end and tapers to a narrower second distal end, wherein the proximal end of the second upper wing partially overlaps the proximal end of the second lower wing to define a combined second wing width substantially equal to the body width; and
   a releasable fastener disposed at the first distal end of each of the first upper wing and the first lower wing, wherein the releasable fastener is adapted to attach the first upper wing to the second upper wing and the first lower wing to the second lower wing to encircle the body part and secure the bag over the body part;
   wherein, when secured by the releasable fasteners, the combination of the first upper wing, the first lower wing, the second upper wing, the second lower wing, the non-expandable wrap body, and the fastening strip produces a focused thermal compression having a compression area corresponding to the fastening strip area, wherein the compression area is adapted to be positioned directly over a desired treatment area of the body part to apply focused thermal compression to the desired treatment area.

2. The wrap of claim 1, wherein the fastening area is 25% or less of the bag area.

3. The wrap of claim 1, wherein the fastening area is 10% or less of the bag area.

4. The wrap of claim 1, further comprising an absorbent material disposed on a contact area of the bag, wherein the absorbent material is adapted to be wettable with water.

5. The wrap of claim 1, wherein each upper wing of the first or second pair of wings is independent of its corresponding lower wing of the first or second pair.

6. The wrap of claim 1, wherein the first and second pairs of wings extend asymmetrically from the wrap body, so that one of the first or second pair of wings is longer that the other of the first or second pair of wings.

7. The wrap of claim 1, further comprising a third pair of expandable, retractable wings extending from the first body end, wherein the third pair of wings is longer than the first pair of wings.

8. The wrap of claim 7, wherein the first pair of wings is adapted to be rolled up and tucked under the third pair of wings.

9. The wrap of claim 1, wherein the first and second pairs of wings are each formed from a laminate having an elastic layer and a non-elastic layer.

10. The wrap of claim 9, wherein the laminate comprises a neck-bonded laminate or a stretch-bonded laminate.

11. The wrap of claim 1, wherein the wrap body and the first and second pairs of wings are integrally formed from a continuous sheet.

12. A wrap for applying a thermal treatment to a body part, comprising:
   a bag adapted for containing a thermal agent, wherein the bag has a bag area;
   a non-expandable wrap body, the wrap body having an end-to-end length and a side-to-side width;
   a fastening means for attaching the bag to the wrap body, the fastening means comprising a strip extending across the side-to-side width of the wrap body, the strip having a fastening area that is 25% or less of the bag area;
   a first pair of wings comprising a first upper wing and a first lower wing formed from an expandable, retractable material and extending from a first end of the wrap body, wherein each of the first upper wing and the first lower wing has a proximal end with a first wing width adjacent the first end of the wrap body and tapers to a narrower first distal end, wherein the proximal end of the first upper wing partially overlaps the proximal end of the first lower wing to define a combined first wing width substantially equal to the side-to-side width, and wherein the expandable, retractable material comprises a laminate having an elastic layer and a non-elastic layer;
   a second pair of wings comprising a second upper wing and a second lower wing formed from an expandable, retractable material and extending from a second end of the wrap body, wherein each of the second upper wing and the second lower wing has a proximal end with a second wing width adjacent the second end of the wrap body and tapers to a narrower second distal end, wherein the proximal end of the second upper wing partially overlaps the proximal end of the second lower wing to define a combined second wing width substantially equal to the body width, and wherein the expandable, retractable material comprises a laminate having an elastic layer and a non-elastic layer; and
   a releasable fastener disposed at the first distal end of each of the first upper wing and the first lower wing, wherein the releasable fastener is adapted to attach the first upper wing to the second upper wing and the first lower wing to the second lower wing to encircle the body part and secure the bag over the body part;

wherein the combination of the first and second pairs of wings, the non-expandable wrap body, and the fastening strip produces a focused thermal compression having a compression area corresponding to the fastening strip area, wherein the compression area is adapted to be positioned directly over a desired treatment area of the body part to apply focused thermal compression to the desired treatment area.

13. The wrap of claim 12, further comprising the third pair of wings extending from the first end of the wrap body, wherein the third pair of wings is longer than the first pair of wings.

14. The wrap of claim 12, wherein the fastening area is located off-center from a lengthwise center of the wrap body.

15. The wrap of claim 12, wherein the laminate comprises a neck-bonded laminate or a stretch-bonded laminate.

16. The wrap of claim 12, wherein the non-expandable wrap body comprises a microporous polymer film.

17. The wrap of claim 12, wherein each wing of the first or second pair of wings is independent of the other wing of the first or second pair.

18. A wrap for applying a thermal treatment to a body part, comprising:
   a bag adapted for containing a thermal agent, wherein the bag has a bag area;
   a non-expandable wrap body comprising a microporous film, the wrap body having a first end and a second end with an end-to-end length and a side-to-side width;
   a fastening means for attaching the bag to the wrap body, the fastening means comprising a strip extending across the side-to-side width of the wrap body, the strip having a fastening area that is 10% to 50% of the bag area;
   a first pair of wings comprising a first upper wing and a first lower wing formed from an expandable, retractable material and extending from the first end of the wrap body, wherein each of the first upper wing and the first lower wing has a proximal end with a first wing width adjacent the first end of the wrap body and tapers to a narrower first distal end, wherein the proximal end of the first upper wing partially overlaps the proximal end of the first lower wing to define a combined first wing width substantially equal to the side-to-side width, and wherein the expandable, retractable material comprises a bonded laminate material having an elastic layer and a non-elastic layer;
   a second pair of wings comprising a second upper wing and a second lower wing formed from an expandable, retractable material and extending from the second end of the wrap body, wherein each of the second upper wing and the second lower wing has a proximal end with a second wing width adjacent the second end of the wrap body and tapers to a narrower second distal end, wherein the proximal end of the second upper wing partially overlaps the proximal end of the second lower wing to define a combined second wing width substantially equal to the body width, and wherein the expandable, retractable material comprises a bonded laminate material having an elastic layer and a non-elastic layer; and
   a releasable fastener disposed at the first distal end of each of the first upper wing and the first lower wing, wherein the releasable fastener is adapted to attach the first upper wing to the second upper wing and the first lower wing to the second lower wing to encircle the body part and secure the bag over the body part;
   wherein the combination of the first and second pairs of wings, the non-expandable wrap body, and the fastening strip produces a focused thermal compression having a compression area corresponding to the fastening strip area, wherein the compression area is adapted to be positioned directly over a desired treatment area of the body part to apply focused thermal compression to the desired treatment area.

19. The wrap of claim 18, wherein the fastening area is centered along a lengthwise center of the wrap body.

20. The wrap of claim 18, wherein each wing of the first or second pair of wings is independent of the other wing of the first or second pair.

* * * * *